United States Patent
Prasad et al.

[11] Patent Number: 6,132,215
[45] Date of Patent: Oct. 17, 2000

[54] HIGH MODULUS HYBRID FIBERS FOR DENTAL RESTORATIONS

[75] Inventors: Arun Prasad, Cheshire; Ajit Karmaker, Wallingford, both of Conn.

[73] Assignee: Jeneric/Pentron Incorporated, Wallingford, Conn.

[21] Appl. No.: 09/060,621

[22] Filed: Apr. 15, 1998

[51] Int. Cl.[7] .................................................. A61C 5/08
[52] U.S. Cl. ..................... 433/220; 433/222.1; 433/180
[58] Field of Search ........................... 433/219, 224, 433/226, 222.1, 191, 220, 221, 180; 132/321

[56] References Cited

U.S. PATENT DOCUMENTS

| | | | |
|---|---|---|---|
| 4,063,838 | 12/1977 | Michael | 403/343 |
| 4,107,845 | 8/1978 | Lee, Jr. et al. | 523/116 |
| 4,717,341 | 1/1988 | Goldberg et al. | 433/9 |
| 4,894,012 | 1/1990 | Goldberg et al. | 433/222.1 |
| 5,328,372 | 7/1994 | Reynaud et al. | 433/221 |
| 5,540,870 | 7/1996 | Quigley | 264/103 |
| 5,564,929 | 10/1996 | Alpert | 433/224 |
| 5,741,139 | 4/1998 | Sicurelli, Jr. et al. | 433/220 |
| 5,797,748 | 8/1998 | Reynaud et al. | 433/224 |
| 5,816,816 | 10/1998 | Scharf | 433/224 |
| 5,829,979 | 11/1998 | Kobashigawa et al. | 433/215 |

FOREIGN PATENT DOCUMENTS

| | | |
|---|---|---|
| 2 573 979 | 6/1986 | France . |
| WO 89 04640 | 1/1989 | WIPO . |
| WO 96 26687 | 6/1996 | WIPO . |

OTHER PUBLICATIONS

Database WPI, Week 8919, Derwent Publications Ltd., GB; AN 89–143298, XP002116596 and SE 8 703 108 A (Ekstrand K), Feb. 11, 1989, Abstract.

*Primary Examiner*—John J. Wilson
*Attorney, Agent, or Firm*—Cantor Colburn LLP

[57] ABSTRACT

A hybrid fiber-reinforced structural component for dental restorations, wherein the hybrid reinforcing fibers comprise a core having a composite sheath bonded thereto. Preferably, the core comprises a material having a high modulus, such as tungsten, tantalum, niobium, boron or carbon. The composite sheath comprises fibers disposed within a polymeric matrix material, preferably the fibers glass or polyethylene fibers. The hybrid fiber-reinforced composite is particularly useful as a structural component for bridges or for reinforcement of a tooth restoration after endodontic treatment.

25 Claims, 1 Drawing Sheet

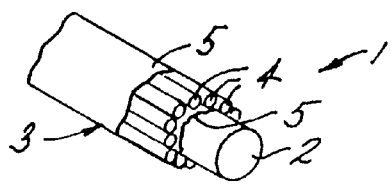
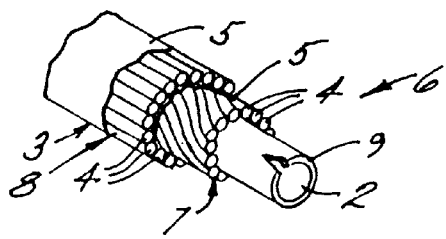
FIG. 1     FIG. 2
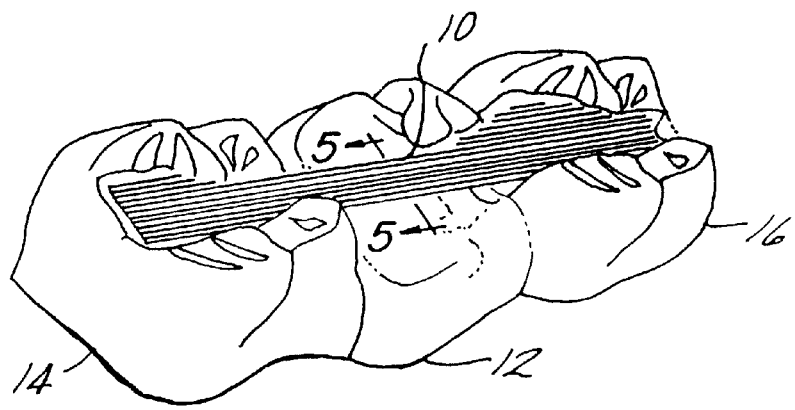
FIG. 3
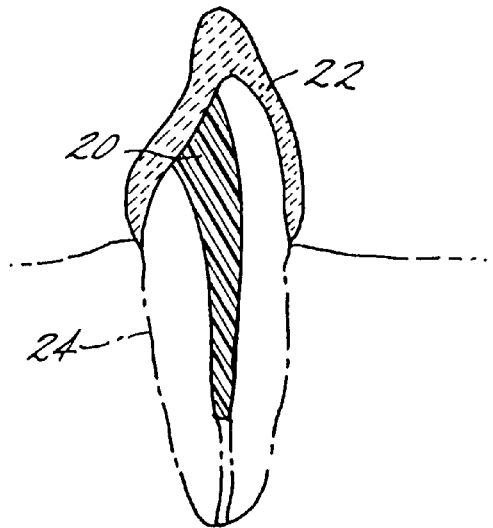
FIG. 4
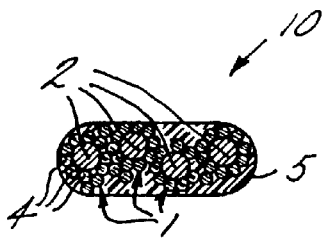
FIG. 5A
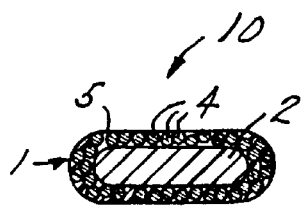
FIG. 5B

HIGH MODULUS HYBRID FIBERS FOR DENTAL RESTORATIONS

BACKGROUND OF THE INVENTION

1. Field of the Invention

This invention relates to reinforcing materials for dental restorations. In particular, this invention relates to fibers for reinforcement of dental restorations, wherein the fibers are high modulus hybrids.

2. Brief Discussion of the Prior Art

Fiber-reinforced composites have found increasing use as structural components in dental restorations, and are described, for example, in U.S. Pat. Nos. 4,717,341 and 4,894,012 to Goldberg et al., as well as U.S. Pat. No. 4,107,845 to Lee, Jr. et al. Fiber-reinforced composites generally comprise at least two components, a polymeric matrix and fibers embedded within the matrix. The polymeric matrix may be selected from those known for use in composite dental materials, for example polyamides, polyesters, polyolefins, polyimides, polyacrylates, polyurethanes, vinyl esters or epoxy-based materials. The fibers used to reinforce composite material may comprises glass, carbon, or polymer fibers such as polyaramide and polyethylene, as well as other natural and synthetic fibers.

Fiber reinforced composite materials provide several advantages, most notably increased strength and stiffness. As described in U.S. Pat. Nos. 4,717,341 and 4,894,012 to Goldberg et al., the contents of which are incorporated herein by reference, such fiber-reinforced composite materials are used as structural components in a variety of dental appliances, taking the form of bars, wires, beams, posts, clasps, and laminates for use in traditional bridges, crowns, artificial teeth, dentures, veneers, and the like. They have also been used in connection with orthodontic retainers, bridges, space maintainers, splints, and the like. In these applications, the fibers preferably take the form of long, continuous filaments, although the filaments may be as short as 3 to 4 millimeters. Shorter fibers of uniform or random length might also be employed. Where the composite structures take the form of elongated wires, the fibers are at least partially aligned and oriented along the longitudinal dimensions of the wire. However, depending on the end use of the composite material, the fibers may also be otherwise oriented, including being normal or perpendicular to that dimension.

Current commercial fiber-reinforced composite materials utilize glass or polyethylene fibers in unidirectional, woven, braided, or mat (non-woven) forms. Glass and polyethylene fibers are currently preferred as being more aesthetic than higher modulus materials. However, the tensile moduli of glass and polyethylene fibers are below 175 GPa. Lower tensile modulus correlates with a lower modulus of elasticity, and thus lower stiffness and greater deflection under load. If the deflection of the structural component exceeds the fracture strain of the overlay or veneer material, the cracking of the latter will result. Thus, while current materials are well-suited for their intended purposes, it would be desirable to use reinforcing fiber materials having a higher tensile modulus, while retaining the aesthetic advantages of glass and polyethylene fibers.

SUMMARY OF THE INVENTION

The above-described drawbacks and deficiencies of the prior art are alleviated by the aesthetic, hybrid reinforcing fibers in accordance with the present invention, wherein the hybrid reinforcing fibers comprise a high modulus core bonded to a sheath comprising aesthetically pleasing fibers embedded within a polymeric matrix. Advantageously, the effective hybrid fiber-reinforced composites of the present invention fall within a range of desirable moduli of elasticity for dental materials, and can be designed and engineered to provide a continuous selection of stiffness and strength over a wide range by adjusting the characteristics of the core material, size, shape and placement of the fibers.

BRIEF DESCRIPTION OF THE DRAWINGS

FIG. 1 is a perspective view in partial section of a hybrid fiber in accordance with the present invention showing a core and composite sheath;

FIG. 2 is a perspective view in partial section of a hybrid fiber showing an alternative composite sheath in accordance with the present invention;

FIG. 3 is a perspective view of a partial bridge using a bar comprising the hybrid fiber-reinforced composite in accordance with the present invention;

FIG. 4 is a section view of a restored endodontically-treated tooth using a post comprising the hybrid fiber-reinforced composite in accordance with the present invention;

FIG. 5A is a cross section view, taken substantially along line 5—5 of FIG. 3, of a bar showing an embodiment of the hybrid fiber-reinforced composite of the present invention; and FIG. 5B is a cross section view, taken substantially along line 5—5 of FIG. 3, of a bar showing an alternative embodiment of the hybrid fiber-reinforced composite of the present invention.

DETAILED DESCRIPTION OF THE INVENTION

The hybrid fibers in accordance with the present invention comprise a high modulus core bonded to a sheath comprising a polymeric matrix and aesthetic reinforcing fibers disposed within the matrix. The hybrid fibers are advantageously used as a structural component for dental restorations such as bridges and endodontically-treated tooth restorations. Thus, referring now to FIG. 1 there is shown an embodiment of a hybrid fiber 1 according the present invention comprising a high modulus core 2 having a sheath 3 bonded thereto. Sheath 3 comprises aesthetic fibers 4 surrounded by polymer matrix 5. In one embodiment sheath 3 is bonded to core 2 using polymer matrix 5. In an alternative embodiment (not shown) a suitable adhesive is utilized to secondarily bond sheath 3 to core 2. Fibers 4 are advantageously comprised of one or a plurality of aesthetically pleasing long continuous fiber such as glass or other translucent material.

Core 2 of the present invention is advantageously comprised of a material having a modulus of about 400 GPa or greater, such as tungsten, tantalum, niobium, boron, and carbon. The use of a high modulus core increases the overall tensile modulus of hybrid fiber 1 over the prior art glass or polyethylene fibers, which have a tensile modulus of about 175 GPa. Although the preferred core materials provide for increased structural properties over the prior art they are typically not aesthetically appealing. In accordance with the present invention aesthetically pleasing fiber reinforced sheath 3 surrounds core 2, thereby providing hybrid fiber 1 with an overall aesthetically acceptable appearance.

The aesthetically pleasing fibers 4 of sheath 3 include, but are not limited to those known in the art, for example polyethylene fibers, polyaramide fibers, and glass fibers, or combinations thereof. The fibers are preferably treated by known methods to improve adhesion with polymeric matrix element 5, for example the polyethylene fibers are plasma-treated, and the glass fibers are abraded and silanized.

As shown in the FIGURES, fibers 4 comprising sheath 3 preferably take the form of long, continuous filaments, although the filaments may be as short as 3 to 4 millimeters. Shorter fibers of uniform or random length might also be employed. Where the fiber bundles take the form of elongated wires, the fibers are at least partially aligned and oriented along the longitudinal dimensions of the wire. However, as discussed in more detail below, depending on the end use of the composite material the fibers within the sheath may also be otherwise oriented, including being normal or perpendicular to that dimension, in the form of layers, a mesh, or a weave. The amount of reinforcing fibers 4 used within sheath 3 will depend on the particular application, but preferably comprises at least about 20% by weight of the composite material. Fibers 4 are preferably completely embedded in polymeric matrix 5, or their outer portions away from core 2 may be partially exposed.

The polymeric matrix element 5 of sheath 3 is selected from those known in the art of dental materials, including but not being limited to polyamides, polyesters, polyolefins, polyimides, polyacrylates, polyurethanes, vinyl esters or epoxy-based materials. Other polymeric matrices include styrene, styrene acrylonitrile, ABS polymers, polysulfones, polyacetals, polycarbonates, polyphenylene sulfides, and the like.

Preferred materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine, all of which are herein incorporated by reference in their entirety. Especially preferred methacrylate monomers include the condensation product of bisphenol A and glycidyl methacrylate, 2,2'-bis [4-(3-methacryloxy-2-hydroxy propoxy)-phenyl]-propane (hereinafter abbreviated "BIS-GMA"), the condensation product of ethoxylated bisphenol A and glycidyl methacrylate (hereinafter EBPA-DMA), and the condensation product of 2 parts hydroxymethyl-methacrylate and 1 part triethylene glycol bis (chloroformate) (hereinafter PCDMA). Polyurethane dimethacrylates (hereinafter abbreviated to PUDMA) are also commonly-used principal polymers suitable for use in the present invention. The polymeric matrix of the sheath is preferably compatible with the polymeric matrix used to build up the restoration around the fiber-reinforced structural component.

The polymeric matrix of the sheath may also be, or further comprise, a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethylmethacrylate, 1,6-hexanedioldimethacrylate, and 2-hydroxypropylmethacrylate; glyceryl dimethacrylate; ethyleneglycolmethacrylates, including ethyleneglycolmethacrylate, diethyleneglycolmethacrylate, triethyleneglycolmethacrylate and tetraethyleneglycol-methacrylate; and diisocyanates, such as 1,6-hexamethylene diisocyanate. Triethyleneglycoldimethacrylate (TEGDMA) is particularly preferred for use in the present invention.

The polymer matrix typically includes polymerization initiators, polymerization accelerators, ultra-violet light absorbers, anti-oxidants, and other additives well known in the art. The polymer matrices may be light curable, self-curing, dual curing, and vacuum, heat, and pressure curable compositions as well as any combination thereof The light curable compositions include the usual polymerization initiators, polymerization accelerators, ultraviolet absorbers, fluorescent whitening agents, and the like. In the self-curing compositions, the polymerization accelerator can be included in the resinous composition which is used for pretreating the exposed dentin. The heat and pressure curable compositions, which are generally filled compositions, include, in addition to the monomeric components, a heat cure initiator such as benzoyl peroxide, 1,1'-azobis (cyclohexanecarbo-nitrile), or other free radical initiators.

In addition to unfilled polymeric matrices, the polymeric matrices of the sheath of the present invention can also be filled or partially filled. The filled compositions of the invention can include all of the inorganic/organic fillers currently used in dental restorative materials, the amount of such filler being determined by the specific function of the filled materials.

The filled compositions of this invention can, in general, include any suitable filler which is capable of being covalently bonded to the polymer matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina zirconia tin oxide and titania. Particularly suitable fillers for dental filing-type materials prepared in accordance with this invention are those having a particle size ranging from about 0.1–5.0 $\mu$m with a silicate colloid of 0.001 to about 0.07 microns and prepared by a series of milling steps comprising wet milling in an aqueous medium surface etch milling and silanizing milling in a silane solution. Some of the aforementioned inorganic filling materials are disclosed in U.S. Pat. Nos. 4,544,359 and 4,547,531, pertinent portions of which are incorporated herein by reference. The filler content in general is in the range from about 0 to about 25% by weight of the total matrix composition, and preferably about 0 to about 10% by weight of the total matrix composition, depending on desired properties of the structural component.

In addition to the aesthetic value of a fiber reinforced sheath 3, the structural performance of hybrid fiber 1 can be tailored by varying the amount and orientation of the fiber bundles with respect to core 2 and the direction of load. In FIG. 1 fibers 4 are shown in a unidirectional orientation along the axis of core 2 thereby providing a maximum tensile modulus to composite fiber 1. An alternative embodiment is shown in FIG. 2 wherein hybrid fiber 6 is shown having composite sheath 3 bonded to core 2 wherein sheath 3 is comprised of a first fiber layer 7 and a second fiber layer 8 surrounded by matrix 5. In the embodiment shown fiber layer 8 performs structurally equivalently to the embodiment shown in FIG. 1 because of its axial alignment with core 2. Fiber layer 7 however is spirally wrapped and individual fiber bundles 4 are aligned at approximately 45 degrees to the axial length of core 2, thereby providing an increase in torsional modulus to hybrid fiber 6. The combination of fiber layers 7, 8 and core 2 provide a hybrid fiber 6 which exhibits increased axial and torsional moduli along with enhance aesthetics over the prior art. Other advantageous properties may be realized by use of fibers 4 arrayed in the form a single or plurality of mesh (or other weave) layers surrounding core 2. While use of fibers such as polyethylene or glass confers aesthetic advantages to the structural components of the present invention, use of fibers 4 comprising tungsten, carbon, or other high-modulus materials is also within the scope of the present invention.

An alternative embodiment of the present invention is also shown in FIG. 2, wherein core 2 is bonded to a suitable coating material 9. Coating material 9 is advantageously comprised of an optically opaque inorganic oxide or organic coating to further provide a masking effect of the underlying core 2. Coating material 9 would preferably be applied to core 2 prior to the bonding of sheath 3 to core 2. One suitable inorganic coating is silicate glass containing opacifiers. A suitable organic coating is dimethacrylate esters mixed with opacifiers such as $TiO_2$ or $ZrO_2$.

Referring now to FIG. 3, a preferred embodiment of a structural component of the present invention is shown, wherein the hybrid fiber reinforced composite is in the form of a bar 10 providing structural support for a bridge 12 between teeth 14, 16. The cross-section of bar 10 may be rectangular, rhomboidal, ovoidal, cylindrical, or of any other cross-sectional configuration effective to provide strength and stiffness to the finished bridge. Bar 10 may be provided to the dentist or technician as a prefabricated composite, or it may be fabricated by the dentist or technician from the hybrid fibers and polymeric matrix.

FIG. 4 shows an alternative embodiment of a structural component according to the present invention, wherein the hybrid fiber reinforced composite is in the form of a post 20 providing structural support for a crown 22 fitted to an endodontically-treated tooth 24. The cross-sectional shape of the post may also be rectangular, rhomboidal, ovoidal, cylindrical, or any other shape effective to provide strength to the tooth restoration. Suitable configurations for posts are well-known in the art.

Post 20 may also be provided to the dentist or technician as a prefabricated composite, or fabricated by the dentist or technician from the hybrid fibers and composite described hereinabove. In a particularly preferred embodiment, the composite post is supplied or formed by the technician and only partially cured, such that the polymeric matrix retains a degree of malleability. The composite post is then fitted to the endodontically treated tooth so as to conform the post to the tooth cavity, and fully cured. This process allows ready "custom-fitting" of a post to any endodontically-treated tooth.

Referring now to FIG. 5A there is shown a cross section of bar 10 of FIG. 3 according to a preferred embodiment of the present invention. In the embodiment shown bar 10 is comprised of four (4) individual hybrid fibers 1 wherein the outside shape of bar 10 is molded by conventional techniques encapsulating the hybrid fibers within resin matrix 5. A particular benefit to the embodiment shown in FIG. 5A is that because of the relatively small diameters of core 2 and inherent flexibility of glass or polyethylene fibers 4, hybrid fibers 1 remain flexible prior to full curing of resin matrix 5. This inherent flexibility allows bar 10, in the precured state, to be easily manipulated and shaped to yield near perfect fit for bar 10 in the final cure state. Bar 10 may therfor also be considered a tape, and used for wrapping, for example wrapping a core for a tooth replacement. An alternative embodiment of bar 10 is shown with reference to FIG. 5B comprising a single hybrid fiber 1. Core 2 comprises a similar shape to that of bar 10 and is bonded to a single or multiple layer(s) of fibers 4 embedded within matrix 5. The outside shape of bar 10 is again molded using conventional composite molding techniques to yield the structure shown in the FIG. 3. Although the embodiment shown in FIG. 5B is not as flexible in the precured state as that shown in FIG. 5A, this particular embodiment will generally yield a bar 10 having superior structural properties in the final cured state for the same cross sectional area.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A structural component for a dental restoration comprising at least one hybrid fiber, said hybrid fiber comprising:
   a core comprising tungsten, tantalum, niobium, boron, or carbon;
   an optically opaque coating bonded to said core; and
   a sheath surrounding said optically opaque coating, said sheath comprising a plurality of fibers disposed within a polymeric matrix, wherein said plurality of fibers are longitudinally aligned with the core.

2. A structural component as set forth in claim 1 wherein said core comprises a material having a tensile modulus greater than 175 GPA.

3. A structural component as set forth in claim 2 wherein said plurality of fibers comprise glass fibers, polyaramide fibers, polyethylene fibers, or combinations thereof.

4. A structural component as set forth in claim 1 wherein said plurality of fibers are aesthetically acceptable fibers for dental restorations.

5. A structural component as set forth in claim 1 wherein said sheath is bonded to said core by an adhesive.

6. A structural component as set forth in claim 1, said structural component having a length greater than its average diameter.

7. A structural component as set forth in claim 6, wherein said structural component is in the shape of a bar for effective strengthening of a bridge.

8. A structural component as set forth in claim 6, wherein said structural component is in the shape of a post for effective strengthening of an endodontically-treated tooth.

9. A structural component for a dental restoration comprising
   at least one hybrid fiber, said hybrid fiber comprising:
      a core comprising tungsten, tantalum, niobium, boron, or carbon; and
      a sheath surrounding said core, said sheath comprising a plurality of fibers disposed within a polymeric matrix, wherein said plurality of fibers are longitudinally aligned with the core, and farther wherein said sheath is bonded to said core by an adhesive.

10. The structural component of claim 9, wherein said core comprises a material having a tensile modulus greater than 175 GPa.

11. A structural component as set forth in claim 9 wherein said plurality of fibers are aesthetically acceptable fibers for dental restorations.

12. A structural component as set forth in claim 11 wherein said plurality of fibers comprise glass fibers, polyaramide fibers, polyethylene fibers, or combinations thereof.

13. A structural component as set forth in claim 9 wherein said sheath is bonded to said core by an adhesive.

14. A structural component as set forth in claim 9, wherein said dental restoration is a bridge.

15. A dental restoration as set forth in claim 9, wherein said structural component is a post for an endodontically-treated tooth.

16. A dental restoration comprising at least one hybrid fiber, said hybrid fiber comprising:
   a core;
   a sheath surrounding said core, said sheath comprising a plurality of fibers disposed within a polymeric matrix, wherein said plurality of fibers are longitudinally aligned with the core, and further wherein said sheath is bonded to said core by an adhesive; and
   a crown or a bridge.

17. The dental restoration as set forth in claim 16, wherein said core comprises a material having a tensile modulus greater than 175 GPA.

18. The dental restoration as set forth in claim 16, wherein said core comprises tungsten, tantalum, niobium, boron, or carbon.

19. The dental restoration as set forth in claim 16, wherein said plurality of fibers are aesthetically acceptable fibers for dental restorations.

20. The dental restoration as set forth in claim 16, wherein said plurality of fibers comprise glass fibers, polyaramide fibers, polyethylene fibers, or combinations thereof.

21. The dental restoration as set forth in claim 16, further comprising an optically opaque coating bonded to said core.

22. A dental restoration comprising at least one hybrid fiber, said hybrid fiber comprising:
   a core;
   an optically opaque coating bonded to said core;
   a sheath surrounding said optically opaque coating, said sheath comprising a plurality of fibers disposed within a polymeric matrix, wherein said plurality of fibers are longitudinally aligned with the core; and
   a crown or bridge.

23. The structural component as set forth in claim 22, wherein said core comprises a material having a tensile modulus greater than 175 GPA.

24. The structural component as set forth in claim 22, wherein said core comprises tungsten, tantalum, niobium, boron, or carbon.

25. The structural component as set forth in claim 22, wherein said plurality of fibers comprise glass fibers, polyaramide fibers, polyethylene fibers, or combinations thereof.

\* \* \* \* \*

UNITED STATES PATENT AND TRADEMARK OFFICE
CERTIFICATE OF CORRECTION

PATENT NO. : 6,132,215　　　　　　　　　　　　　　　　　　　　　　Page 1 of 1
DATED      : October 17, 2000
INVENTOR(S) : Arun Prasad et al.

It is certified that error appears in the above-identified patent and that said Letters Patent is hereby corrected as shown below:

<u>Column 4,</u>
Line 4, after "thereof" insert -- . --

<u>Column 7,</u>
Line 1, after "A" delete "dental restoration" and insert therefor -- structural component --
Line 2, after "said" delete "structural component" and insert therefor -- dental restoration --

Signed and Sealed this

First Day of June, 2004

JON W. DUDAS
*Acting Director of the United States Patent and Trademark Office*